United States Patent [19]

Harders et al.

[11] 4,143,080

[45] Mar. 6, 1979

[54] METHOD AND REAGENT FOR THE ASSAY OF HYDROPEROXIDE

[75] Inventors: Hans-Dieter Harders; Roland Helger, both of Darmstadt, Fed. Rep. of Germany

[73] Assignee: The Goodyear Tire & Rubber Company, Akron, Ohio

[21] Appl. No.: 850,523

[22] Filed: Nov. 11, 1977

[30] Foreign Application Priority Data

Nov. 25, 1976 [DE] Fed. Rep. of Germany ....... 2653537

[51] Int. Cl.$^2$ ............................................. G01N 33/16
[52] U.S. Cl. ........................... 23/230 B; 195/103.5 R; 195/103.5 C; 252/408
[58] Field of Search ............... 23/230 B; 195/103.5 R, 195/103.5 C; 252/408

[56] References Cited

U.S. PATENT DOCUMENTS

| | | | |
|---|---|---|---|
| 3,016,292 | 1/1962 | Bauer et al. ............... | 195/103.5 C X |
| 3,266,868 | 8/1966 | Marvill ...................... | 195/103.5 C X |
| 3,335,069 | 8/1967 | Wachter ..................... | 23/230 B X |
| 3,404,069 | 10/1968 | Ware ......................... | 195/103.5 C |
| 3,654,180 | 4/1972 | Bauer ........................ | 195/103.5 C X |
| 4,040,908 | 8/1977 | Clark, Jr. ................... | 195/103.5 C X |

FOREIGN PATENT DOCUMENTS

| | | |
|---|---|---|
| 1598828 | 4/1971 | Fed. Rep. of Germany. |
| 2163421 | 7/1973 | Fed. Rep. of Germany. |
| 2264847 | 5/1975 | Fed. Rep. of Germany ......... 23/230 B |

OTHER PUBLICATIONS

Malmstadt et al.; "A New Automatic Spectrophotometric Rate Method for Selective Determination of Glucose in Serum, Plasma or Blood"; Analytical Chemistry, vol. 34, No. 4, Apr. 1962, pp. 452–455.

*Primary Examiner*—Morris O. Wolk
*Assistant Examiner*—Arnold Turk
*Attorney, Agent, or Firm*—J. Y. Clowney

[57] ABSTRACT

In a method for detection and/or assay of hydroperoxides (or, indirectly, of substances, such as cholesterol or glucose, which react to liberate hydroperoxides) using an assay reagent comprising a water-soluble iodide, a redox catalyst and a stabilizer, an improvement is provided wherein when the determination is made in the presence of protein, the redox catalyst concentration in the reagent is 5–500 $\mu$M and the stabilizer concentration in the reagent is 5–100 mg/l. A corresponding improvement in the assay reagent is also provided.

9 Claims, No Drawings

METHOD AND REAGENT FOR THE ASSAY OF HYDROPEROXIDE

BACKGROUND OF THE INVENTION

The present invention relates to a method and an agent for the photometric detection and assay of hydroperoxides per se, or indirectly, of substances which react to liberate hydroperoxides, in liquids containing proteins.

The determination of hydroperoxides, in particular hydrogen peroxide, plays an important part in clinical chemistry. Many enzymatic substrate determinations are carried out with oxidases. For example, cholesterol is assayed with cholesterol oxidase; glucose is assayed with glucose oxidase; aminoacids are assayed with aminoacid oxidase; uric acid is assayed with uricase and the like. The hydrogen peroxide formed in amounts equimolar with those of the substance being assayed in these reactions, can be determined in a known manner electrochemically or photometrically. The electrochemical processes are disadvantageous because they require special apparatus and tend to be unreliable. Photometric methods of determination are preferred and more widely used.

One of the most widely known photometric methods of determination is based on the oxidation of certain chromogens by hydrogen peroxide with the aid of a catalyst to produce a dyestuff whose presence is detected photometrically. Peroxidase and the systems, iodide/molybdate (German Auslegeschrift No. 1,284,124), iodide/vanadate (German Offenlegungsschrift No. 1,598,828) and iodide/tungstate (German Offenlegungsschrift No. 2,163,421) are known as such catalysts in connection with glucose determinations.

In another method of glucose determination (Anal. Chem. 34, 452 (1962)), the triiodide formed in the presence of the catalyst system iodide/molybdate, is directly measured photometrically without using a chromogen. This method has the advantage over the chromogen-based methods in that the high extinction coefficient of the triiodide (about 20 cm$^2$/$\mu$M) can be utilized in the spectrophotometric determination, whereby high precision is achieved. At the same time, interference caused by concomitant colored substances in the sample is minimized. In addition, the reagent solution is very stable and can therefore be stored at room temperature, and the use of carcinogenic and cocarcinogenic chromogens can be avoided.

The decisive disadvantage of this method is that the body fluid samle to be investigated must be deproteinized beforehand because, otherwise, the coloration of the triiodide is not stable. However, the time-consuming deproteinization not only makes the determination more difficult, but in cases in which deproteinization is not possible, this requirement renders the otherwise advantageous method inapplicable. One such case is the determination of cholesterol in body fluids since the cholesterol is bound protein.

SUMMARY OF THE INVENTION

Accordingly, it is an object of the present invention to provide a method and an agent for the photometric determination of hydroperoxides in liquids containing proteins.

It is another object of this invention to provide such an agent and method which do not require previous deproteinization of the protein-containing sample being tested.

It is a further object of this invention to provide such an agent and method which are based on the measurement of triiodide and provide very accurate quantitative assays having high precision.

Upon further study of the specification and appended claims, further objects and advantages of this invention will become apparent to those skilled in the art.

The objects of this invention have been achieved by employing amounts of the conventional catalyst system which are orders of magnitude lower than conventionally used concentrations, together with a stabilizer.

Thus, in a method aspect, the present invention provides in a method for the photometric detection and assay, in the presence of protein, of hydroperoxides per se, or indirectly of substances which react to liberate hydroperoxides, using an assay reagent of a water-soluble iodide, a redox catalyst and a stabilizer, the improvement which comprises employing the redox catalyst in a concentration of 5–500 $\mu$M, together with 5–100 mg/l of at least one stabilizer.

In a composition aspect, this invention provides a reagent for use in the photometric determination, in the presence of protein, of hydroperoxides per se, or indirectly of substances which react to liberate hydroperoxides, comprising 5–500 $\mu$M of a redox catalyst, 5–100 mg/l of at least one stabilizer, and a water soluble iodide.

DETAILED DISCUSSION

Surprisingly, a stable coloration of the triiodide in the sample solution is achieved, even in body fluids which have not been deproteinized, by the use of the low catalyst concentration of this invention and by the addition of at least one stabilizer. The stabilizer stabilizes the triiodide ion which is formed during the assay. Further surprisingly, this effect only occurs when both the catalyst and the stabilizer are combined in the concentration ranges required by this invention. Unless otherwise indicated herein, all conditions and/or materials, conventional in the prior art hydroperoxide assay by determination of triiodide ion, are suitable for use in this invention.

Suitable redox catalysts for use in this invention include the sodium, potassium or ammonium salts of molybdic acid (molybdates, $MoO_4^{-2}$), tungstic acid (tungstates, $WO_4^{-2}$) or vanadic acid (vanadates, $VO_4^{-3}$), preferably ammonium molybdate. The catalyst concentrations of this invention are in the range of 5–500 $\mu$M, ammonium molybdate preferably being used in a concentration range of 5–50 $\mu$M, in particular at a concentration of about 10 $\mu$M. The preferred range when using sodium tungstate is 50–200 $\mu$M, and when using sodium vanadate is 50–500 $\mu$M. In the case of the preferred ammonium molydbate catalyst, for example, the concentration used in this invention is orders of magnitude lower than that used in the state of the art (1–10 mM).

Suitable stabilizers for use in this invention include sodium azide, hexamethylenetetramine, potassium fluoride, potassium thiocyanate, ethylenediaminetetraacetic acid and/or nitrilotriacetic acid, preferably sodium azide. It is possible to employ the stabilizers alone or in mixtures. The stabilizer concentration should be in the range of 5–100 mg/l of reagent, preferably 5–50 mg/l. The most preferred concentration is about 10 mg/l of reagent. Generally, the stabilizer concentration should be 0.01–2.0 mM.

Sodium iodide, potassium iodide, ammonium iodide, or a mixture thereof is preferably used as the water-soluble iodide. Potassium iodide is particularly well suited because it is not hydroscopic. Suitable water-soluble iodide concentrations are 0.03–0.2 M, preferably 0.1–0.15 M.

In order to enable the enzymatic reactions to proceed in an optimum pH range, the reagent should also contain buffer substances which maintain the pH in the range of 6.0–7.5. Suitable buffers are fully conventional and include the customary buffers, such as phosphate buffer, citrate buffer, borate buffer or tris-(hydroxymethyl)-aminomethane buffer. Typically, 0.1–0.5 M of buffer per liter of reagent is used.

The process of this invention is suitable for the determination of hydrogen peroxide. Consequently, it is particularly useful in the detection and assay of substances which react under suitable conditions to form hydrogen peroxide, and of substances having a peroxidic action, in liquids containing proteins. It is particularly suitable in cases in which previous deproteinization of the test liquid to be analyzed is not possible, e.g., because the substance to be detected is bound to protein. An important example of such a substance is cholesterol in blood or serum.

In the enzymatic determination of cholesterol, the cholesterol and its esters must be liberated from the lipoproteins. This can be effected, for example, by a protease or by treatment with certain detergents, bile acids or detergents together with bile acids. A detergent is also necessary in order to keep the liberated cholesterol and its esters in solution. For this purpose, a detergent combination of polyethylene glycol mono-(1,1,3,3-tetramethylbutyl)-phenyl ether (1–3 g/l) and alkyldimethylbenzylammonium chloride (0.02–0.2 g/l) has proved particularly suitable for the determination of cholesterol in accordance with this invention. This detergent combination is advantageous in comparision with other detergents useful in this connection, in that it virtually does not increase the blank value of the reagent, and in that addition of bile acid, which inhibits cholesterol oxidase, can be avoided. In addition, the decomposition of the lipoproteins takes place even at room temperature when alkyldimethylbenzylammonium chloride is used; however, higher temperatures and consequently larger decompositions are necessary when other conventional detergents are used.

Within the scope of the preferred combination of reagents, a particularly suitable reagent for cholesterol determination by the process of this invention consists of a buffer/color reagent solution and an enzyme solution:

Buffer/Color Reagent Solution

10–30 g/l of potassium iodide,
5–50 $\mu$M of ammonium molybdate,
5–15 mg/l of sodium azide,
2 g/l of polyethylene glycyol mono-(1,1,3,3-tetramethylbutyl)-phenyl ether,
0.1 g/l of alkyldimethylbenzylammonium chloride and
0.1–0.5 M of buffer of pH 6.2.

Enzyme Solution 0.2–0.6 U/ml of cholesterol esterase and
0.3–1.0 U/ml of cholesterol oxidase.

The procedure for carrying out the process of this invention is conventional. A serum sample is mixed with the buffer/color reagent solution and a measured portion of the enzyme solution is added. After an incubation time of about 15 to 45 minutes at a conventionally suitable temperature, the extinction of the sample is measured at 366 nm against the blank value.

In the case of a glucose determination, the enzyme solution consists of glucose oxidase; in the case of an aminoacid determination it consists of aminoacid oxidase, in the case of uric acid determination it consists of uricase and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Determination of hydrogen peroxide in a solution containing proteins

Buffer/Color Reagent Solution 20 g/l of potassium iodide,
2.0 g/l of polyethylene glycol mono-(1,1,3,3-tetramethylbutyl)-phenyl ether,
0.1 g/l of alkyldimethylbenzylammonium chloride,
10 $\mu$M of ammonium molybdate,
10 mg/l of sodium azide and
0.2 M of potassium phosphate buffer of pH 6.2.

5 ml of the buffer/color reagent solution are mixed with 20 $\mu$l of serum containing hydrogen peroxide; the mixture is incubated at 30° C. for 20 and 40 minutes and the extinction is then measured at 366 nm. 100% of the amount of hydrogen peroxide in the serum sample is detected.

The process is repeated with various ammonium molybdate concentrations and various combinations of ammonium molybdate and sodium azide. The Table which follows shows the results obtained, expressed as the percent of the amount of hydrogen peroxide in the sample which was detected.

| Experiment | Ammonium molybdate [$\mu$M] | Sodium azide [mg/l] | Detected [%] After 20 minutes | Detected [%] After 40 minutes |
|---|---|---|---|---|
| 1 | 1,000 | 1,000 | 0 | 0 |
| 2 | — | — | 83 | 86 |
| 3 | 1,000 | — | 89 | 88 |
| 4 | 10 | — | 96 | 95 |
| 5 | 10 | 10 | 100 | 100 |

The above results show that under the conditions used, only the combination used in accordance with this invention ensures a sufficiently rapid reaction and a stable coloration and is therefore suitable for use in a quantitative determination.

Analogous results are obtained when 100 $\mu$M of sodium tungstate or 200 $\mu$M of sodium vanadate, for example, are employed instead of 10 $\mu$M of ammonium molybdate, and when sodium azide is replaced by hexamethylenetetramine, potassium fluoride, potassium thiocyanate, ethylenediaminetetraacetic acid and/or nitrilotriacetic acid.

EXAMPLE 2

Determination of Cholesterol in Serum

The buffer/color reagent solution is the same as that described in Example 1. The enzyme solution consists of 0.4 U/ml of cholesterol esterase and 0.6 U/ml of cholesterol oxidase.

5 ml of the buffer/color reagent solution are mixed with 20 µl of serum of a known cholesterol concentration. 50 µl of the enzyme solution are pipetted into 1 ml of this mixture and mixed, and the mixture is incubated at 30° C. for 20 and 40 minutes. The extinction of the sample is then measured at 366 nm against a blank value. 100% of the amount of cholesterol in the sample is detected.

The cholesterol content of the serum is calculated as follows:

cholesterol content [mg/100 ml] = ΔE . 440.

The calibration factor is determined by measurements with a primary standard and ΔE is the appropriate photometric signal strength.

Analogously to Example 1, the process is repeated with various concentrations of ammonium molybdate in various mixtures with sodium azide. The Table which follows shows the results obtained, expressed as the percent of the cholesterol in the sample which was detected.

| Experiment | Ammonium molybdate [µM] | Sodium azide [mg/l] | Detected [%] After 20 minutes | Detected [%] After 40 minutes |
|---|---|---|---|---|
| 1 | 1,000 | 1,000 | 0 | 0 |
| 2 | — | — | 91 | 98 |
| 3 | 1,000 | — | 92 | 90 |
| 4 | 10 | — | 93 | 91 |
| 5 | 10 | 10 | 100 | 100 |

The above results show that under the conditions used, only the combination used in accordance with this invention ensures a sufficiently rapid reaction and a stable coloration and therefore is suitable for use in a quantitative cholesterol determination.

Analogous results are obtained in a glucose determination using glucose oxidase, an aminoacid determination using aminoacid oxidase and a uric acid determination using uricase.

EXAMPLE 3

Determination of Glucose in a Solution Containing Proteins

The reactions solution contains the buffer/color reagent solution described in Example 1 and 10 U/ml of glucose oxidase. The glucose containing samples were diluted 1 and 10 times with physiologic serum. 1 ml of the reaction solution is mixed with 50 µl of the diluted sample of a known glucose concentration and the mixture is incubated at 25° C. The extinction of the sample is then measured at 366 nm. The glucose content of the sample is calculated by comparison with a primary glucose standard (2.0 g/l) as follows:

$$\text{glucose content of the sample [g/l]} = \frac{2.0 \times \text{extinction of the sample}}{\text{extinction of the standard}}$$

After different incubation times, the stability of the coloration was investigated by measuring the extinction of 5 different samples:

| Incubation time [min.] | Glucose concentration [g/l] in sample 1 | 2 | 3 | 4 | 5 |
|---|---|---|---|---|---|
| 15 | 0.896 | 0.950 | 0.979 | 1.064 | 2.223 |
| 20 | 0.903 | 0.952 | 0.982 | 1.077 | 2.218 |
| 25 | 0.900 | 0.958 | 0.991 | 1.079 | 2.216 |
| 30 | 0.904 | 0.959 | 0.992 | 1.087 | 2.212 |

The samples 2 and 3 were commercial control sera, containing a glucose concentration of 0.95 and 0.988 [g/l], respectively, according to different reference methods.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. In a process for the photometric determination of hydroperoxides per se in a protein-containing body fluid, or indirectly of substances therein which react to liberate hydroperoxides, using an assay reagent comprising a water-soluble iodide, a redox catalyst and stabilizer, the improvement wherein the concentration of the redox catalyst in the reagent is 5–500 µM, and the concentration of stabilizer is 5–100 mg/l whereby the body fluid does not require deproteinization before the photometric determination.

2. The improvement of claim 1, wherein the redox catalyst is a molybdate, tungstate or vanadate.

3. The improvement of claim 2, wherein 5–50 µM of ammonium molybdate is the redox catalyst.

4. The improvement of claim 1, wherein sodium azide, hexamethylenetetramine, potassium fluoride, potassium thiocyanate, ethylenediaminetetraacetic acid, nitrilotriacetic acid or a mixture thereof is the stabilizer.

5. In a process for the photometric determination in a protein-containing body fluid of hydrogen peroxide liberated from cholesterol treated with cholesterol oxidase, using an assay reagent comprising a water-soluble iodide, a redox catalyst and stabilizer, the improvement wherein the concentration of the redox catalyst in the reagent is 5–500 µM, and the concentration of stabilizer is 5–100 mg/l whereby the body fluid does not require deproteinization before the photometric determination.

6. The improved process of claim 5, wherein the determination is carried out in the presence of polyethylene glycol mono-(1,1,3,3-tetramethylbutyl)-phenyl ether and alkyldimethylbenzylammonium chloride.

7. In a reagent for the photometric determination of hydroperoxides per se or indirectly of substances which react to liberate hydroperoxides, comprising a water-soluble iodide, a redox catalyst and stabilizer, the improvement wherein the concentration of redox catalyst is 5–500 µM and the concentration of stabilizer is 5–100 mg/l.

8. The improvement of claim 7, wherein the redox catalyst is 5–50 µM of ammonium molybate, the stabilizer is 10 mg/l of sodium azide and the soluble iodide is potassium iodide.

9. A method of detecting and assaying hydroperoxide in the presence of protein which comprises photometrically measuring the amount of triiodide ion formed when a reagent comprising water-soluble iodide, a redox catalyst in a concentration of 5–500 µM and stabilizer in a concentration of 5–100 mg/l is mixed with a protein- and hydroperoxide-containing test specimen.

* * * * *

UNITED STATES PATENT AND TRADEMARK OFFICE
CERTIFICATE OF CORRECTION

PATENT NO. : 4,143,080
DATED : March 6, 1979
INVENTOR(S) : HANS-DIETER HARDERS ET AL It is certified that error appears in the above—identified patent and that said Letters Patent are hereby corrected as shown below:

Assignee: reads "The Goodyear Tire & Rubber Company, Akron, Ohio ".

should read -- MERCK PATENT GESELLSCHAFT MIT BESCHRANKTER HAFTUNG, Darmstadt, Federal Republic of Germany -- .

Attorney, Agent, or Firm: reads "J.Y. Clowney".

should read -- MILLEN & WHITE -- .

Signed and Sealed this

Fifteenth Day of July 1980

[SEAL]

Attest:

SIDNEY A. DIAMOND

Attesting Officer

Commissioner of Patents and Trademarks